(12) United States Patent
Sato et al.

(10) Patent No.: US 9,570,985 B2
(45) Date of Patent: Feb. 14, 2017

(54) INTELLIGENT GATE DRIVE VOLTAGE GENERATOR

(75) Inventors: Tetsuo Sato, San Jose, CA (US); Jim Comstock, Fremont, CA (US); Ryotaro Kudo, Takasaki (JP); Masashi Koyano, Takasaki (JP)

(73) Assignee: Renesas Electronics America Inc., Santa Clara, CA (US)

( * ) Notice: Subject to any disclaimer, the term of this patent is extended or adjusted under 35 U.S.C. 154(b) by 639 days.

(21) Appl. No.: 12/829,975

(22) Filed: Jul. 2, 2010

(65) Prior Publication Data

US 2012/0001608 A1   Jan. 5, 2012

(51) Int. Cl.
G05F 1/00 (2006.01)
H02M 3/158 (2006.01)
H02M 1/00 (2006.01)

(52) U.S. Cl.
CPC ... *H02M 3/1588* (2013.01); *H02M 2001/0019* (2013.01); *H02M 2001/0022* (2013.01); *Y02B 70/1466* (2013.01)

(58) Field of Classification Search
CPC ............................. G05F 1/59; H02M 2001/0045
USPC ........ 323/271, 269, 272, 282–287, 289, 290
See application file for complete search history.

(56) References Cited

U.S. PATENT DOCUMENTS

| | | | | |
|---|---|---|---|---|
| 5,627,460 A | * | 5/1997 | Bazinet | G05F 1/618 323/224 |
| 5,847,554 A | * | 12/1998 | Wilcox | H02M 3/1588 323/282 |
| 7,215,108 B2 | * | 5/2007 | Inn | H02M 1/36 323/285 |
| 7,345,463 B2 | * | 3/2008 | Isham | 323/285 |
| 2003/0016545 A1 | * | 1/2003 | Jutras | H02M 3/1588 363/18 |
| 2005/0083025 A1 | * | 4/2005 | Brown | H02M 3/158 323/283 |
| 2006/0038547 A1 | * | 2/2006 | Ahmad | H02M 1/08 323/284 |
| 2008/0007241 A1 | * | 1/2008 | Isham | H02M 1/08 323/285 |
| 2008/0012546 A1 | * | 1/2008 | Nagaya | H02M 3/1588 323/282 |
| 2008/0061756 A1 | * | 3/2008 | Shirai | H02M 3/1588 323/282 |
| 2008/0258697 A1 | * | 10/2008 | Gehrke | H02M 3/1588 323/283 |
| 2008/0259651 A1 | | 10/2008 | Huynh et al. | 363/21.12 |

(Continued)

FOREIGN PATENT DOCUMENTS

JP   2007-509593   4/2007   ............ H02M 3/155

*Primary Examiner* — Adolf Berhane
*Assistant Examiner* — Gary Nash
(74) *Attorney, Agent, or Firm* — Campbell Stephenson LLP

(57) ABSTRACT

According to an embodiment of the invention, an apparatus includes a microprocessor-based pulse-width modulation controller configured to generate a pulse-width modulation signal, and a synchronous converter including a first transistor, a second transistor, a first driver, and a second driver. The apparatus further includes a drive voltage generator configured to generate a drive voltage for the synchronous converter. The drive voltage generator is further configured to generate the drive voltage based on a measured output current and a measured input voltage.

18 Claims, 9 Drawing Sheets

(56) References Cited

U.S. PATENT DOCUMENTS

| | | | |
|---|---|---|---|
| 2008/0278123 A1* | 11/2008 | Mehas | H02M 3/1588 323/266 |
| 2008/0290848 A1* | 11/2008 | Nguyen | H02M 3/156 323/282 |
| 2008/0309608 A1* | 12/2008 | Shen | G09G 3/3696 345/101 |
| 2009/0323375 A1 | 12/2009 | Galvana et al. | 363/21.06 |
| 2010/0001704 A1 | 1/2010 | Williams | 323/283 |

* cited by examiner

Q1 - High Side MOSFET
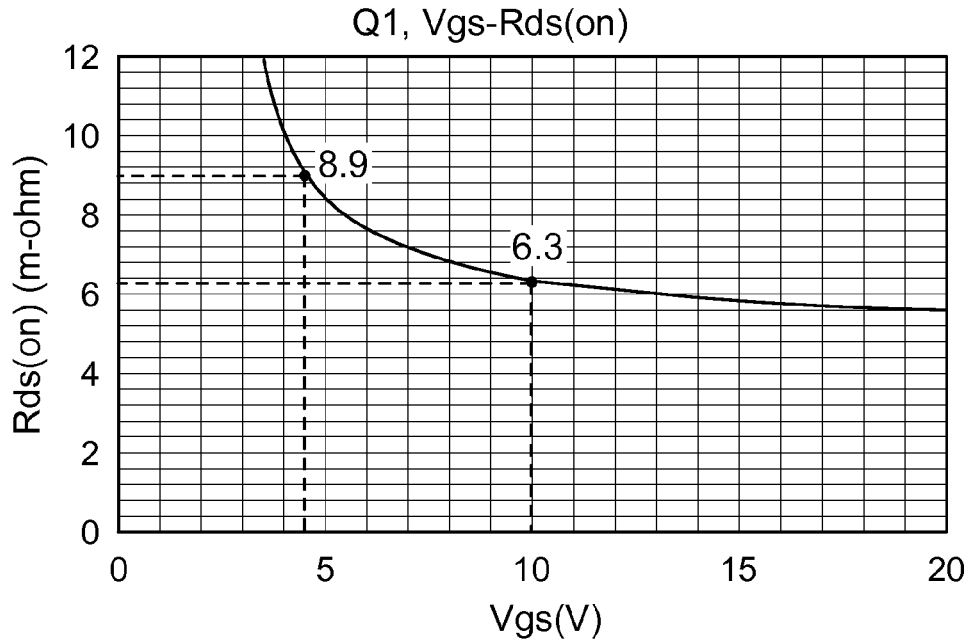
Fig.4 Q1 - Vgs Vs. Rds
Q2 - Low Side MOSFET
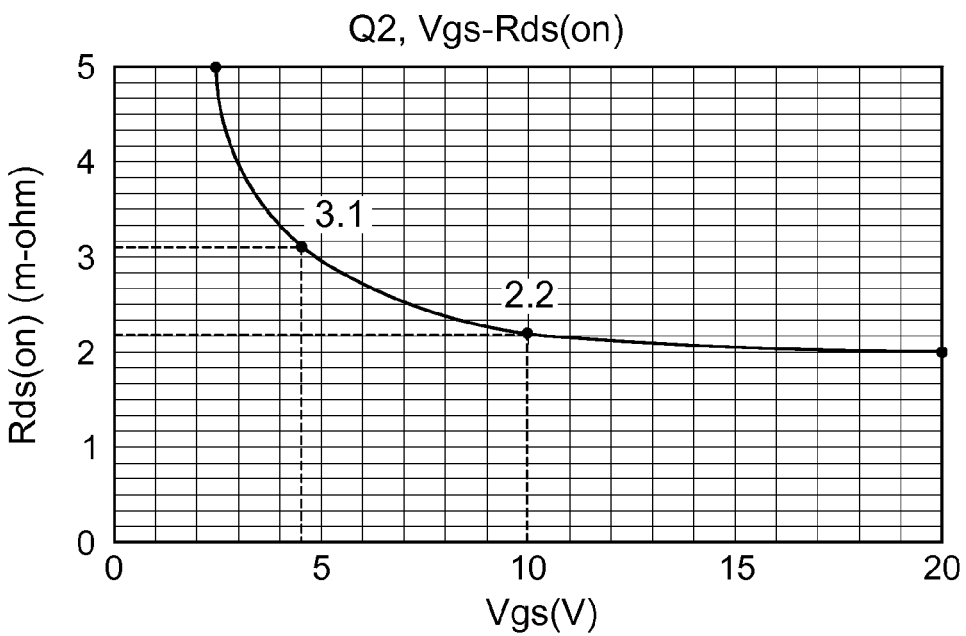
Fig.5 Q2 - Vgs Vs. Rds

INTELLIGENT GATE DRIVE VOLTAGE GENERATOR

BACKGROUND

Field

Embodiments of the present invention generally relate to electronic systems. More specifically, certain embodiments of the present invention relate to voltage regulator systems.

Description of the Related Art

In computer systems, components, such as a central processing unit ("CPU") or graphics processing unit ("GPU") require power to operate. However, in general, a component of a computer system does not realize all of the power generated by a power supply, and a power loss can occur. Thus, in computer systems, it is important for the computer system's power supply to be efficient to minimize power loss.

Furthermore, in general, a computer system requires an efficient operation during both heavy load operations, and light-load operations, such as when the computer system is in a standby mode. This is especially important in a notebook personal computer ("NBPC"), also known as a laptop computer, which includes a battery, because an efficient operation maximizes the operation time of the battery.

SUMMARY

According to an embodiment of the invention, an apparatus includes a microprocessor-based pulse-width modulation controller configured to generate a pulse-width modulation signal, and a synchronous converter. The apparatus further includes a drive voltage generator configured to generate a drive voltage for the synchronous converter. The drive voltage generator is further configured to generate the drive voltage based on a measured output current and a measured input voltage.

According to another embodiment of the invention, a method includes configuring a voltage regulator system to comprise a microprocessor-based pulse-width controller and a synchronous converter, and measuring an output current and an input voltage. The method further includes determining a drive voltage based on the measured output current and the measured input voltage, and generating, using a drive voltage generator, the drive voltage for the voltage regulator system.

BRIEF DESCRIPTION OF THE DRAWINGS

Further embodiments, details, advantages, and modifications of the present invention will become apparent from the following detailed description of the preferred embodiments, which is to be taken in conjunction with the accompanying drawings, wherein:

FIG. 4 illustrates a graph which correlates a gate source voltage with a saturation resistance for a high-side metal-oxide-semiconductor field-effect transistor.

FIG. 5 illustrates a graph which correlates a gate source voltage with a saturation resistance for a low-side metal-oxide-semiconductor field-effect transistor.

DETAILED DESCRIPTION

It will be readily understood that the components of the present invention, as generally described and illustrated in the figures herein, may be arranged and designed in a wide variety of different configurations. Thus, the following detailed description of the embodiments of a method and apparatus, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more embodiments.

Throughout this specification, measurement symbols are used, consistent with their ordinary usage as understood by one of ordinary skill in the relevant art. For sake of clarity, the following measurement symbols, utilized throughout this specification, are defined herein:

A=ampere
H=henry
Hz=hertz
Ω=ohm
V=volt
W=watt

In a NBPC system, a component, such as a CPU or GPU, requires an efficient operation with a power source, such as a battery. A voltage regulator system is configured to regulate a voltage provided to the NBPC system in order to minimize power loss and maximize power efficiency. However, as will be discussed below in more detail, it has been determined that a drive voltage (also identified as a gate source voltage; as one of ordinary skill in the art would readily appreciate, the terms "drive voltage" and "gate source voltage" are used interchangeably in this specification) can be varied in order to reduce the total power loss, and thus, increase power efficiency, depending on such whether the NBPC system is performing high-load operations or low-load operations. Thus, according to an embodiment of the invention, a voltage regulator system can be provided, which includes a drive voltage generator, where the drive voltage generator is configured to generate a drive voltage based on factors including an output current and an input voltage. Thus, according to the embodiment, the drive voltage can be varied in order to minimize power loss and maximize power efficiency.

Figure 1:
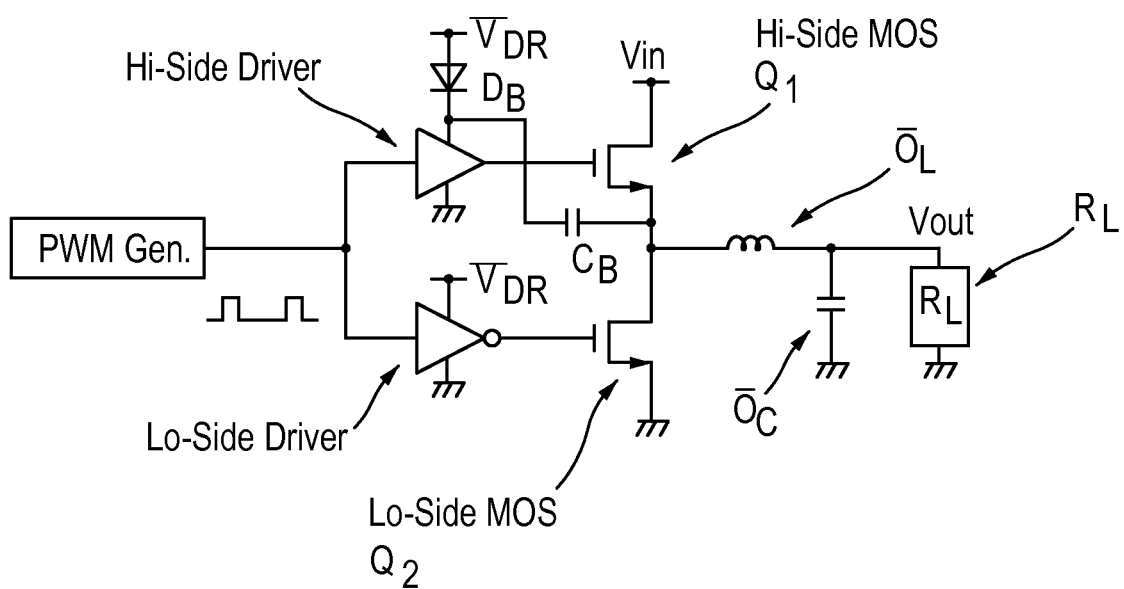
FIG. 1 illustrates a block diagram of a direct-current to direct-current converter for a personal computer.
Figure 2:
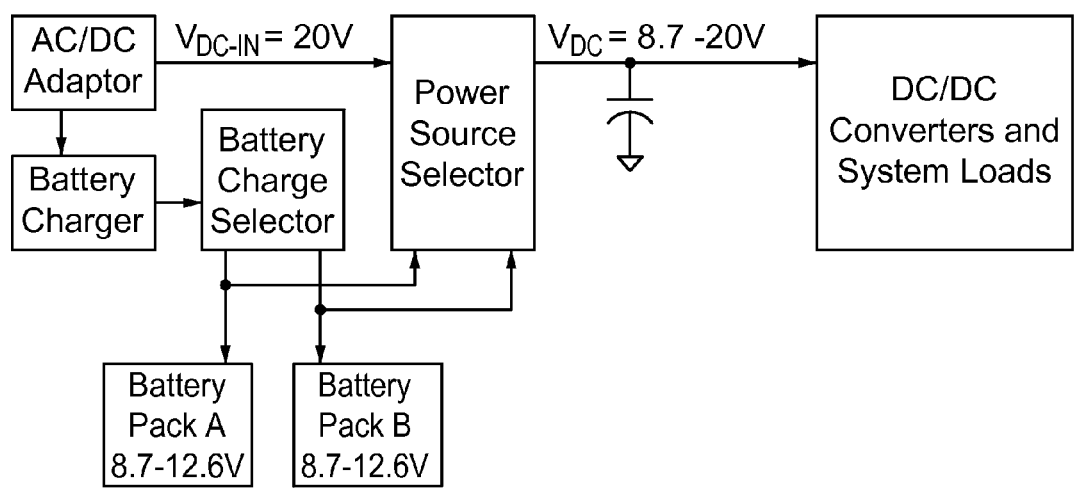
FIG. 2 illustrates a block diagram of a power delivery system for a notebook personal computer.

The structural components of a non-isolated direct-current to direct-current converter and a power delivery system are described in relation to FIGS. 1 and 2. Subsequently, the relationship involving an input voltage, an output current, a drive voltage, and an overall power loss is described in relation to FIGS. 3, 4, and 5. Next, embodiments of the present invention which utilize a variable drive voltage generation are described in relation to FIGS. 6 and 7. Finally, enhanced efficiencies which are realized in embodiments of the present invention are described in relation to FIGS. 8 and 9.

FIG. 1 illustrates a block diagram of a direct-current to direct-current ("DC-DC") converter for a personal computer, such as a NBPC. The DC-DC converter illustrated in FIG. 1 is a synchronous step-down DC-DC converter, also known as a synchronous buck converter, configured to receive an input voltage (identified in FIG. 1 as "$V_{IN}$") and produce an output voltage (identified in FIG. 1 as "$V_{OUT}$") using a drive voltage (identified in FIG. 1 as "$V_{DR}$"), where the output voltage is lower than the input voltage. One reason for the usage of a step-down DC-DC converter is when the voltage needed by a component is less than the voltage provided by a power supply. For example, a CPU or GPU generally requires a voltage which is lower than a voltage produced by an alternate current ("AC"), adapter or a battery, such as a lithium ion battery. A step-down DC-DC converter can convert a voltage produced by the AC adapter or battery, to a voltage that can be consumed by the CPU or GPU.

As illustrated in FIG. 1, the DC-DC converter includes a pulse-width modulation ("PWM") generator (identified in FIG. 1 as "PWM Gen") configured to generate a PWM signal. The DC-DC converter also includes a high-side driver (identified in FIG. 1 as "Hi-Side Driver"), a low-side driver (identified in FIG. 1 as "Lo-Side Driver"), a high-side metal-oxide-semiconductor field-effect transistor ("MOSFET") (identified in FIG. 1 as "Hi-Side MOS"), and a low-side MOSFET (identified in FIG. 1 as "Lo-Side MOS").

An example of the low-side MOSFET and the high-side MOSFET is an n-channel MOSFET. A n-channel MOSFET generally needs a significant positive charge applied to the n-channel MOSFET in order to turn the n-channel MOSFET on. Thus, the DC-DC converter also includes a bootstrap circuit configured to generate a significant voltage to turn on the high-side MOSFET. Specifically, the bootstrap circuit includes diode "$D_B$" and capacitor "$C_B$". Together, diode $D_B$ and capacitor $C_B$ can create a voltage $V_{DR}+V_{IN}$, which the high-side driver can use to turn on the high-side MOSFET. The DC-DC converter also includes output inductor "$\overline{O}_L$" which is configured to generate the voltage output of the high-side MOSFET and the low-side MOSFET as voltage $V_{OUT}$.

FIG. 2 illustrates a block diagram of a power delivery system for a notebook personal computer ("NBPC"). The power delivery system includes an AC/DC adapter (identified in FIG. 2 as AC/DC Adapter), a battery charger (identified in FIG. 2 as Battery Charger), a battery charge selector (identified in FIG. 2 as Battery Charge Selector), two battery packs (identified in FIG. 2 as Battery Pack A and Battery Pack B), a power source selector (identified in FIG. 2 as Power Source Selector), and one or more DC-DC converters, with each DC-DC converter operably connected to one or more system loads, such as a CPU or a GPU (identified in FIG. 2 as DC-DC Converters and System Loads). In an embodiment of the invention, the one or more DC-DC converters can be a synchronous DC-DC converter, similar to the synchronous DC-DC converter illustrated in FIG. 1. While the block diagram of FIG. 2 illustrates a power deliver system which includes two battery packs, one of ordinary skill in the art would readily appreciate that the power delivery system can include a single battery pack, or any other number of battery packs.

The AC/DC adapter is configured to produce a voltage (identified in FIG. 2 as $V_{DC-IN}$) that can be used to either charge one or both of the battery packs, or to provide voltage to the one or more DC-DC converters. In the example block diagram illustrated in FIG. 2, the voltage produced by AD/DC is 20V. However, this is merely an example voltage. In one mode, the one or more DC-DC converters are configured to receive voltage from the AC/DC adapter. In another mode, when the AC/DC adapter is not used to provide voltage to the one or more DC-DC converters, the one or more DC-DC converters are configured to receive voltage from either battery pack A or battery pack B. In the example block diagram illustrated in FIG. 2, the voltage produced by battery pack A and battery pack B is within a range of 8.7-12.6V, depending on a fuel condition of the battery, which is a typical range for a battery. However, this is merely an example range. For example, when a battery is at a low level, the battery generally produces 7.9V of voltage. In both modes, the voltage received by the one or more DC-DC converters (identified in FIG. 2 as $V_{DC}$) is received via the power source selector. As illustrated in the example block diagram, the range of the voltage received by the one or more DC-DC converters can range anywhere from 8.7-20V. As one of ordinary skill in the art would readily appreciate, this is a exemplary range. As described above, a DC-DC converter can be a synchronous DC-DC converter, and can include a high-side MOSFET and a low-side MOSFET, and the one or more DC-DC converters are configured to produce an output voltage at a fixed voltage, such as 1V. Thus, a duty cycle for the high-side MOSFET and the low-side MOSFET changes based on the input voltage which can range anywhere from 7.6-12.6V.

Figure 3:
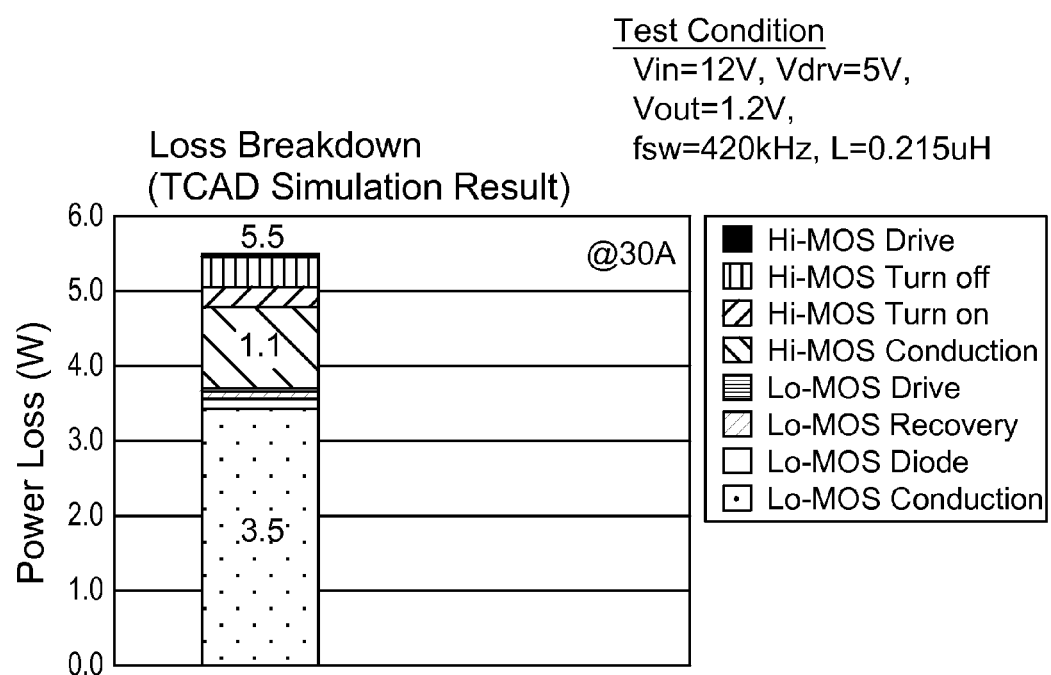
FIG. 3 illustrates a loss breakdown of the direct-current to direct-current converter of FIG. 1 under simulated conditions.

FIG. 3 illustrates a loss breakdown of the direct-current to direct-current ("DC-DC") converter of FIG. 1 under simulated conditions. As described above, the DC-DC converter illustrated in FIG. 1 is a synchronous step-down DC-DC converter, which is configured to receive an input voltage and produce an output voltage, where the output voltage is lower than the input voltage. During this process, voltage (also identified as power) can be lost, which reduces the efficiency of the DC-DC converter. Voltage can be lost for a number of reasons, such as excess voltage dissipating as heat. Therefore, in order to maintain good efficiency, one must minimize the power loss in the DC-DC converter, and specifically, the power loss in the high-side MOSFET and low-side MOSFET of the DC-DC converter. FIG. 3, as will be described in more details, shows a breakdown of the power loss of the DC-DC converter of FIG. 1 under simulated conditions.

As illustrated in FIG. 3, the test conditions include an input voltage being input to the DC-DC converter ("Vin") of 12V, a drive voltage being generated within the DC-DC converter ("Vdrv") of 5V, an output voltage that is generated by the DC-DC converter ("Vout") of 1.2V, a switching frequency of a PWM generator of the DC-DC converter ("fsw") of 420 kHz, a DC-DC converter inductance of 0.215

μH, and an output current that is generated by the DC-DC converter of 30 A. As one of ordinary skill in the art would readily appreciate, a duty cycle of a high-side MOSFET equals a total output voltage divided by a total input voltage. Thus, the test conditions illustrated in FIG. 3 also include a high-side duty cycle of 0.1 or 10%.

According to FIG. 3, the total power loss of the DC-DC converter under the test conditions is 5.5 W. The total power loss is broken down into the following categories: Hi-MOS Drive, Hi-MOS Turn off, Hi-MOS Turn on, Hi-MOS Conduction, Lo-MOS Drive, Lo-MOS Recovery, Lo-MOS Diode, and Lo-MOS Conduction. As can be seen in FIG. 3, the largest components of the total power loss are Hi-MOS Conduction, at 1.1 W, and Lo-MOS Conduction, at 3.5 W. Hi-MOS conduction refers to the conduction of a current through a conductive channel of the high-side MOSFET, and Lo-MOS conduction refers to the conduction of a current through a conductive channel of the low-side MOSFET.

While the largest component of the total power loss with respect to the high-side MOSFET is the Hi-MOS Condition, other components of the total power loss are Hi-MOS Turn off and Hi-MOS Turn on. Hi-MOS Turn off and Hi-MOS Turn on refer to a switching loss that can occur when the high-side MOSFET is turned on and off. A switching loss is a power loss that occurs when a MOSFET is switched from an off state to an on state, and vice-versa. Thus, in order to minimize the power loss in the DC-DC converter, one must consider the switching loss of an high-side MOSFET, and a conduction loss of a low-side MOSFET.

The power loss illustrated in FIG. 3 can be dependent on a drive voltage of the DC-DC converter. For example, while the drive voltage of the test conditions illustrated in FIG. 3 is 5V, a higher drive voltage can result in a lower conduction loss, also identified as a lower saturation resistance ("Rds (on)"). This lower conduction loss results in lower overall power loss, as shown in FIG. 3. As another example, while the input voltage of the test conditions illustrated in FIG. 3 is 12V, a lower input voltage can result in a lower switching loss, because the switching loss is consumed by a capacitor of the DC-DC converter. This lower switching results in lower overall power loss, as shown in FIG. 3. Furthermore, the power loss illustrated in FIG. 3 can depend on conditions other than the input voltage, such as output current, switching frequency, and temperature. Thus, different test conditions can result in different loss allocations.

As described above, a total power loss for a high-side MOSFET is based, in part, on a conduction loss for the high-side MOSFET. A conduction loss for a high-side MOSFET can be calculated using the following general equation:

$$PconductionHS = Iout^2 \cdot RdsonHSatVgsHS \cdot DutyHS$$

In the above general equation, PconductionHS represents a conduction loss for a high-side MOSFET, Iout represents an output current, RdsonHSatVgsHS represents a saturation resistance of a high-side MOSFET, at a given drive voltage of the high-side MOSFET, and DutyHS represents a duty cycle of a high-side MOSFET. Thus, in order to calculate a conduction loss for a high-side MOSFET, an output current, a saturation resistance of a high-side MOSFET, and a duty cycle of a high-side MOSFET must be known. Methods for calculating a duty cycle of a high-side MOSFET and a saturation resistance of a high-side MOSFET will now be described.

As described above, a duty cycle for a high-side MOSFET equals a total output voltage divided by a total input voltage. In other words, a duty cycle for a high-side MOSFET can be calculated using the following general equation:

$$DutyHS = Vout/Vin$$

In the above general equation, Vout represents an output voltage, and Vin represents an input voltage. For example, when an output voltage equals 1V and an input voltage equals 8V, the duty cycle equals 1V/8V or 0.125. However, when an input voltage is increased from 8V to 20V, the duty cycle equals 1V/20V or 0.05. Thus, by increasing the input voltage from 8V to 20V, a duty cycle of a high-side MOFET is decreased from 0.125 to 0.05 for a fixed value of a saturation resistance and output current of the high-side MOSFET.

Turning to saturation resistance, as one of ordinary skill in the art would readily appreciate, a saturation resistance of an element is a measure of its opposition to the passage of a steady electric current. Thus, a lower saturation resistance of an element indicates a lower overall power loss of the element, and thus, indicates a higher efficiency in conducting a current through the element. As described above, a saturation resistance can be represented as "Rds(on)." Thus, a low Rds(on) value indicates a low saturation resistance value. A saturation resistance for a high-side MOSFET is a function of a drive voltage that is applied to a gate of the high-side MOSFET, which will be demonstrated in relation to FIG. 4.

FIG. 4 illustrates a graph which correlates a gate source voltage with a saturation resistance for a high-side MOSFET. Specifically, FIG. 4 illustrates a graph with an x-axis of drive voltage values, also identified as gate source voltage ("Vgs") values, for a high-side MOSFET, and a y-axis of Rds(on) values for a high-side MOSFET. The curve of the graph indicates a correlation of Vgs values with Rds(on) values. For example, when a Vgs for a high-side MOSFET is 5V, a Rds(on) for the high-side MOSFET is 8.0 m-Ω, or 0.008Ω. However, when the Vgs for the high-side MOSFET is increased from 5V to 10V, the Rds(on) for the high-side MOSFET is reduced to 6.3 m-Ω, or 0.0063Ω. Thus, as can be seen from the graph illustrated in FIG. 4, as Vgs is increased for the high-side MOSFET, Rds(on) is reduced.

A method for calculating a conduction loss for a high-side MOSFET using a duty cycle value and a saturation resistance value will now be described using specific input voltage and gate source voltage values. The high-side MOSFET's conduction loss can be determined for input voltage values of 8V and 20V, for an output voltage value of 1V, for gate source voltage values of 5V and 10V, and for an output current of 30 A.

For an output current of 30 A, an input voltage of 8V, an output voltage of 1V, and a gate source voltage of 5V and 10V, the following calculations can be performed to determine the high-side duty cycle:

Iout=30 A

Vin=8V

Vout=1V

DutyHS(8)=Vout/Vin

DutyHS(8)=1V/8V

DutyHS(8)=0.125

When the gate source voltage is 5V, then the corresponding saturation resistance can be determined using the graph illustrated in FIG. 3:

RdsonHS(5V)=0.008Ω

A high-side conduction loss when the gate source voltage is 5V can now be calculated using the above-calculated duty cycle and the saturation resistance:

$$PconductionHS(5V) = Iout^2 \cdot RdsonHS(5V) \cdot DutyHS \quad (8)$$

$$PconductionHS(5V) = (30\ A)^2 \cdot 0.008\Omega \cdot 0.125$$

$$PconductionHS(5V) = 0.9\ W$$

Thus, the high-side conduction loss is 0.9 W, when the gate source voltage is 5V, the input voltage is 8V, the output voltage is 1V, and the output current is 30 A.

When the gate source voltage is 10V, then the corresponding saturation resistance can also be determined using the graph illustrated in FIG. 4:

$$RdsonHS(10V) = 0.0063\Omega$$

A high-side conduction loss when the gate source voltage is 10V can also now be calculated using the above-calculated duty cycle and the saturation resistance:

$$PconductionHS(10V) = Iout^2 \cdot RdsonHS(10V) \cdot DutyHS \quad (8)$$

$$PconductionHS(10V) = (30\ A)^2 \cdot 0.0063\Omega \cdot 0.125$$

$$PconductionHS(10V) = 0.70875\ W$$

Thus, at an input voltage of 8V, it can be seen that increasing the gate source voltage from 5V to 10V lowers the conduction loss of the high-side MOSFET from 0.9 W to 0.70875 W.

Next, for an output current of 30 A, an input voltage of 20V rather than 8V, an output voltage of 1V, and a gate source voltage of 5V and 10V, a duty cycle can be calculated as follows:

$$Iout = 30A$$

$$Vin = 20V$$

$$Vout = 1V$$

$$DutyHS(20) = Vout/Vin$$

$$Duty\ HS(20) = 1V/20V$$

$$DutyHS(20) = 0.05$$

As previously described, when the gate source voltage is 5V, a corresponding saturation resistance is 0.008Ω, and when the gate source voltage is 10V, a corresponding saturation resistance is 0.0063Ω. A high-side conduction loss when the gate source voltage is 5V can now be calculated using the above-calculated duty cycle and the saturation resistance:

$$PconductionHS(5V) = Iout^2 \cdot RdsonHS(5V) \cdot DutyHS \quad (20)$$

$$PconductionHS(5V) = (30\ A)^2 \cdot 0.008\Omega \cdot 0.05$$

$$PconductionHS(5V) = 0.36\ W$$

Thus, the high-side conduction loss is 0.36 W, when the gate source voltage is 5V, the input voltage is 20V, the output voltage is 1V, and the output current is 30 A.

A high-side conduction loss when the gate source voltage is 10V can also now be calculated using the above-calculated duty cycle and the saturation resistance:

$$PconductionHS(10V) = Iout^2 \cdot RdsonHS(10V) \cdot DutyHS \quad (20)$$

$$PconductionHS(10V) = (30\ A)^2 \cdot 0.0063\Omega \cdot 0.05$$

$$PconductionHS(10V) = 0.2835\ W$$

Thus, at an input voltage of 20V, it can be seen that increasing the gate source voltage from 5V to 10V lowers the conduction loss of the high-side MOSFET from 0.36 W to 0.2835 W. Furthermore, it can be seen that increasing the input voltage from 8V to 20V significantly lowers the conduction loss of the high-side MOSFET from the 0.70875 W-0.9 W range to the 0.2835 W-0.36 W range. The high-side conduction loss when varying a gate source voltage and an input voltage is summarized in the following table:

| Vin | Cond. Loss when Vgs = 5 V | Cond. Loss when Vgs = 10 V | Delta | Iout | Vout | Duty Cycle |
|---|---|---|---|---|---|---|
| 8 V | 0.9 W | 0.709 W | −0.191 W | 30 A | 1 V | 0.125 |
| 20 V | 0.36 W | 0.284 W | −0.077 W | 30 A | 1 V | 0.05 |

Similar to a high-side MOSFET, a total power loss for a low-side MOSFET is based, in part, on a conduction loss for the low-side MOSFET. A conduction loss for a low-side MOSFET can be calculated using the following general equation:

$$PconductionLS = Iout^2 \cdot RdsonLSatVgsLS \cdot DutyLS$$

In the above general equation, PconductionLS represents a conduction loss for a low-side MOSFET, Iout represents an output current, RdsonLSatVgsLS represents a saturation resistance of a low-side MOSFET, at a given drive voltage of the low-side MOSFET, and DutyLS represents a duty cycle of a low-side MOSFET. Thus, in order to calculate a conduction loss for a low-side MOSFET, an output current, a saturation resistance of a low-side MOSFET, and a duty cycle of a low-side MOSFET must be known. Methods for calculating a duty cycle of a low-side MOSFET and a saturation resistance of a low-side MOSFET will now be described.

With respect to duty cycle, a duty cycle for a low-side MOSFET equals one minus a total output voltage divided by a total input voltage. In other words, a duty cycle for a low-side MOSFET can be calculated using the following general equation:

$$DutyLS = 1 - (Vout/Vin)$$

In the above general equation, similar to the general equation to calculate a duty cycle for a high-side MOSFET, Vout represents an output voltage, and Vin represents an input voltage. For example, when an output voltage equals 1V and an input voltage equals 8V, the duty cycle equals 1−(1V/8V) or 0.875. When an input voltage is increased from 8V to 20V, the duty cycle equals 1−(1V/20V) or 0.95. Thus, by increasing the input voltage from 8V to 20V, a duty cycle of a low-side MOFET is increased from 0.875 to 0.95 for a fixed value of a saturation resistance and output current of the low-side MOSFET.

Turing to saturation resistance, as described previously with respect to a high-side MOSFET, a saturation resistance for a low-side MOSFET is a function of a drive voltage that is applied to a gate of the low-side MOSFET, which will be demonstrated in relation to FIG. 4.

FIG. 5 illustrates a chart which correlates a gate source voltage with a saturation resistance for a low-side MOSFET. Specifically, FIG. 5 illustrates a graph with an x-axis of drive voltage values, also identified as gate source voltage ("Vgs") values, for a low-side MOSFET, and a y-axis of Rds(on) values for a low-side MOSFET. The curve of the graph indicates a correlation of Vgs values with Rds(on) values. For example, when a Vgs for a low-side MOSFET is 5V, a Rds(on) for the low-side MOSFET is 3.1 m-Ω, or 0.0031Ω. However, when the Vgs for the low-side MOSFET is increased from 5V to 10V, the Rds(on) for the high-side MOSFET is reduced to 2.2 m-Ω, or 0.0022Ω. Thus, as can be seen from the graph illustrated in FIG. 5, as Vgs is increased for the low-side MOSFET, Rds(on) is reduced.

A method for calculating a conduction loss for a low-side MOSFET using a duty cycle value and a saturation resistance value will now be described using specific input voltage and gate source voltage values. The low-side MOSFET's conduction loss can be determined for input voltage values of 8V and 20V, for an output voltage value of 1V, for gate source voltage values of 5V and 10V, and for an output current of 30 A.

For an output current of 30 A, an input voltage of 8V, an output voltage of 1V, and a gate source voltage of 5V and 10V, the following calculations can be performed to determine the low-side duty cycle:

Iout=30 A

Vin=8V

Vout=1V

DutyLS(8)=1·(Vout/Vin)

DutyLS(8)=1·(1V/8V)

DutyLS(8)=0.875

The corresponding saturation resistance, for a gate source voltage of 5V and 10V, can be determined using the graph illustrated in FIG. 5:

RdsonLS(5V)=0.0031Ω

RdsonLS(10V)=0.0022Ω

A low-side conduction loss when the gate source voltage is 5V can now be calculated using the above-calculated duty cycle and the saturation resistance:

PconductionLS(5V)=Iout$^2$·RdsonLS(5V)·DutyLS(8)

PconductionLS(5V)=(30 A)$^2$·0.0031Ω·0.875

PconductionLS(5V)=2.44125 W

In addition, a low-side conduction loss when the gate source voltage is 10V can now be calculated using the above-calculated duty cycle and the saturation resistance:

PconductionLS(10V)=Iout$^2$·RdsonLS(10V)·DutyLS(8)

PconductionLS(10V)=(30 A)$^2$·0.0022Ω·0.875

PconductionLS(10V)=1.7325 W

The change in low-side conduction loss due to a change in the gate source voltage from 5V to 10V can be calculated as follows:

DeltaConductionLoss=(PconductionLS(5V)−PconductionLS(10V))

DeltaconductionLoss=(2.44125 W−1.7325 W)

DeltaconductionLoss=0.70875 W

PercentReductionfor5Vto10V=(DeltaconductionLoss/PconductionLS(5V))·100

PercentReductionfor5Vto10V=(0.70875 W/2.44125 W)

PercentReductionfor5Vto10V=29.03226%

Thus, at an output current of 30 A, an input voltage of 8V, and an output voltage of 1V, the low-side conduction loss for a gate source voltage of 5V is 0.70875 W higher than the low-side conduction loss for a gate source voltage of 10V. Thus, a 29.03226% reduction in low-side conduction loss is realized if a gate source voltage of 10V is applied to a low-side gate rather than a gate source voltage of 5V.

Next, for an output current of 30 A, an input voltage of 20V rather than 8V, an output voltage of 1V, and a gate source voltage of 5V and 10V, a duty cycle can be calculated as follows:

Iout=30 A

Vin=20V

Vout=1V

DutyLS(20)=1·(Vout/Vin)

DutyLS(20)=1·(1V/20V)

DutyLS(20)=0.95

As previously described, when the gate source voltage is 5V, a corresponding saturation resistance is 0.0031Ω, and when the gate source voltage is 10V, a corresponding saturation resistance is 0.0022Ω. A low-side conduction loss when the gate source voltage is 5V can now be calculated using the above-calculated duty cycle and the saturation resistance:

PconductionLS(5V)=Iout$^2$·RdsonLS(5V)·DutyLS(20)

PconductionLS(5V)=(30 A)$^2$·0.0031Ω·0.95

PconductionLS(5V)=2.6505 W

In addition, a low-side conduction loss when the gate source voltage is 10V can now be calculated using the above-calculated duty cycle and the saturation resistance:

PconductionLS(10V)=Iout$^2$·RdsonLS(10V)·DutyLS(20)

PconductionLS(10V)=(30 A)$^2$·0.0022Ω·0.95

PconductionLS(10V)=1.881 W

The change in low-side conduction loss due to a change in the gate source voltage from 5V to 10V can be calculated as follows:

DeltaConductionLoss=(PconductionLS(5V)−PconductionLS(10V))

DeltaconductionLoss=(2.6505 W−1.881 W)

DeltaconductionLoss=0.7695 W

PercentReductionfor5Vto10V=(DeltaconductionLoss/PconductionLS(5V))·100

PercentReductionfor5Vto10V=(0.7695 W/2.6505 W)

PercentReductionfor5Vto10V=29.03226%

Thus, at an output current of 30 A, an input voltage of 20V, and an output voltage of 1V, the low-side conduction loss for a gate source voltage of 5V is 0.7695 W higher than the low-side conduction loss for a gate source voltage of 10V. Thus, a 29.03226% reduction in low-side conduction loss is realized if a gate source voltage of 10V is applied to a low-side gate rather than a gate source voltage of 5V. However, increasing the input voltage from 8V to 20V does not change the delta conduction loss at an input current of 30 A. In other words, the low-side conduction loss saving at an output currency of 30 A is still 29.03226%.

While the conduction loss of a MOSFET has been described in great detail, the conduction loss is only a component of a total power loss of a MOSFET. Another component of a total power loss of a MOSFET is a gate drive loss. The gate drive losses for a high-side MOSFET and a low-side MOSFET are generally not the same since they are different MOSFET devices, and, as will be described in more detail, each MOSFET's total gate drive power is a function of each MOSFET's total gate charge, when each MOSFET gate is driven at a specific gate source voltage and a specific switching frequency.

A general equation for determining a MOSFET's total gate drive power is as follows:

Ptotalgatedrive=Vgs·Qg·fs

In the above general equation, Ptotalgatedrive represents a total gate drive loss for a MOSFET, Qg represents a total gate charge for a MOSFET, and fs represents a switching frequency for a MOSFET. A total gate charge for a MOSFET will vary depending upon the gate source voltage of the MOSFET. In the case of a high-side MOSFET, the total gate charge values for a gate source voltage of 5V, and a gate source voltage of 10V, are as follows:

QgHS5=1·10$^{-8}$ (when Vgs=5V)

QgHS10=2·10$^{-8}$ (when Vgs=10V)

For a constant switching frequency, and a gate source voltage of 5V, the following calculations can be performed to determine a total gate drive loss for a high-side MOSFET:

fs=250,000 Hz

VgsHS(5V)=5V

QgHS(5V)=1·10$^{-8}$

PtotalgatedriveHS(5V)=VgsHS(5V)·QgHS(5V)·fs

PtotalgatedriveHS(5V)=(5V)·(1·10$^{-8}$)·(250,000 Hz)

PtotalgatedriveHS(5V)=0.0125 W

For a constant switching frequency, and a gate source voltage of 10V rather than 5V, the following calculations can be performed to determine a total gate drive loss for a high-side MOSFET:

fs=250,000 Hz

VgsHS(10V)=10V

QgHS(10V)=2·10$^{-8}$

PtotalgatedriveHS(10V)=VgsHS(10V)·QgHS(10V)·fs

PtotalgatedriveHS(10V)=(10V)·(2·10$^{-8}$)·(250,000 Hz)

PtotalgatedriveHS(10V)=0.05 W

Once the total gate drive loss for the high-side MOSFET has been calculated, a conduction loss for the high-side MOSFET can also be calculated using the equations described above. For example, given a constant frequency of 250,000 Hz, an output current of 30 A, an input voltage of 12V, an output voltage of 1V, and a gate source voltage of 5V, the conduction loss can be calculated as follows:

DutyHS12=Vout/Vin

DutyHS12=1V/12 V

DutyHS12=0.08333

RdsonHS(5V)=0.008Ω

PconductionHS(5V)=Iout$^2$·RdsonHS(5V)·DutyHS12

PconductionHS(5V)=(30 A)$^2$·(0.008Ω)·(0.08333)

PconductionHS(5V)=0.6 W

As another example, given the above values, but with a gate source voltage of 10V rather than 5V, the conduction loss can be calculated as follows:

DutyHS12=0.08333

RdsonHS(10V)=0.0063Ω

PconductionHS(10V)=Iout$^2$·RdsonHS(10V)·DutyHS12

PconductionHS(10V)=(30 A)$^2$·(0.0063Ω)·(0.08333)

PconductionHS(10V)=0.4725 W

In both the case of a 5V gate source voltage and the case of a 10V gate source voltage, a conduction loss and total gate drive loss for a high-side MOSFET can be combined as follows:
For gate source voltage of 5V:

CombinedHSLosses(5V)=PconductionHS(5V)+PtotalgatedriveHS(5V)

CombinedHSLosses(5V)=0.6 W+0.0125 W

CombinedHSLosses(5V)=0.6125 W

For gate source voltage of 10V:

CombinedHSLosses(10V)=PconductionHS(10V)+PtotalgatedriveHS(10V)

CombinedHSLosses(10V)=0.4725 W+0.05 W

CombinedHSLosses(10V)=0.5225 W

A power loss difference can be calculated by determining a difference of the combined losses at a gate source voltage of 5V and the combined losses at a gate source voltage of 10V as follows:

PowerLossDifferenceHS=CombinedHSLosses(5V)−CombinedHSLosses(10V)

PowerLossDifferenceHS=0.6125 W−0.5225 W

PowerLossDifferenceHS=0.09 W

Thus, as can be seen from the above equations, after combining the conduction loss and total gate drive loss of a high-side MOSFET, the combined losses for the high-side MOSFET are reduced by 0.09 W when the applied high-side gate source voltage is equal to 10V rather than 5V.

Next, determining a total gate drive loss and a conduction loss for a low-side MOSFET will be described. More specifically, examples will now be described where a total grate drive loss and a conduction loss for a low-side MOSFET are calculated for output currents of 30 A and 5 A, an input voltage of 12V, and output voltage of 1V, a switching frequency of 250,000 Hz, and gate source voltages of 5V and 10V.

A total gate charge for a MOSFET will vary depending upon the gate source voltage of the MOSFET. In the case of a low-side MOSFET, the total gate charge values for a gate source voltage of 5V, and a gate source voltage of 10V, are as follows:

$$QgLS5 = 25 \cdot 10^{-9} \text{ (when Vgs=5V)}$$

$$QgLS10 = 55 \cdot 10^{-9} \text{ (when Vgs=10V)}$$

For a constant switching frequency, and a gate source voltage of 5V, the following calculations can be performed to determine a total gate drive loss for a low-side MOSFET:

$$fs = 250,000 \text{ Hz}$$

$$VgsLS(5V) = 5V$$

$$QgLS(5V) = 25 \cdot 10^{-9}$$

$$PtotalgatedriveLS(5V) = VgsLS(5V) \cdot QgLS(5V) \cdot fs$$

$$PtotalgatedriveLS(5V) = (5V) \cdot (25 \cdot 10^{-9}) \cdot (250,000 \text{ Hz})$$

$$PtotalgatedriveLS(5V) = 0.03125 \text{ W}$$

Once the total gate drive loss for the low-side MOSFET has been calculated for a gate source voltage of 5V, a conduction loss for the low-side MOSFET can also be calculated as follows:

$$Iout = 30A$$

$$RdsonLS(5V) = 0.003 \Omega$$

$$DutyLS12 = 1 - (Vout/Vin)$$

$$DutyLS12 = 1 - (1V/12V)$$

$$DutyLS12 = 0.91667$$

$$PconductionLS(5V) = Iout^2 \cdot RdsonLS(5V) \cdot DutyLS12$$

$$PconductionLS(5V) = (30 \text{ A})^2 \cdot (0.003 \Omega) \cdot (0.91667)$$

$$PconductionLS(5V) = 2.475 \text{ W}$$

A conduction loss and total gate drive loss for a low-side MOSFET can be combined as follows:

$$CombinedLSLosses(5V) = PconductionLS(5V) + PtotalgatedriveLS(5V)$$

$$CombinedLSLosses(5V) = 2.475 \text{ W} + 0.03125 \text{ W}$$

$$CombinedLSLosses(5V) = 2.50625 \text{ W}$$

For a constant switching frequency, and a gate source voltage of 10V rather than 5V, the following calculations can be performed to determine a total gate drive loss for a low-side MOSFET:

$$fs = 250,000 \text{ Hz}$$

$$VgsLS(10V) = 10V$$

$$QgLS(10V) = 55 \cdot 10^{-9}$$

$$PtotalgatedriveLS(10V) = VgsLS(10V) \cdot QgLS(10V) \cdot fs$$

$$PtotalgatedriveLS(10V) = (10V) \cdot (55 \cdot 10^{-9}) \cdot (250,000 \text{ Hz})$$

$$PtotalgatedriveLS(10V) = 0.1375 \text{ W}$$

Once the total gate drive loss for the low-side MOSFET has been calculated for a gate source voltage of 10V, a conduction loss for the low-side MOSFET can also be calculated as follows:

$$Iout = 30 \text{ A}$$

$$RdsonLS(10V) = 0.0022 \Omega$$

$$DutyLS12 = 1 - (Vout/Vin)$$

$$DutyLS12 = 1 - (1V/12 \text{ V})$$

$$DutyLS12 = 0.91667$$

$$PconductionLS(10V) = Iout^2 \cdot RdsonLS(5V) \cdot DutyLS12$$

$$PconductionLS(10V) = (30 \text{ A})^2 \cdot (0.0022 \Omega) \cdot (0.91667)$$

$$PconductionLS(10V) = 1.815 \text{ W}$$

A conduction loss and total gate drive loss for a low-side MOSFET can be combined as follows:

$$CombinedLSLosses(10V) = PconductionLS(10V) + PtotalgatedriveLS(10V)$$

$$CombinedLSLosses(10V) = 1.815 \text{ W} + 0.1375 \text{ W}$$

$$CombinedLSLosses(10V) = 1.9525 \text{ W}$$

The power loss difference that occurs when a gate is driven by a gate source voltage of 5V versus a gate source voltage of 10V can be calculated as follows:

$$LossDifference = CombinedLSLosses(5V) - CombinedLSLosses(10V)$$

$$LossDifference = 2.50625 \text{ W} - 1.9525 \text{ W}$$

$$LossDifference = 0.55375 \text{ W}$$

Thus, at an output current of 30 A, an input voltage of 12V, an output voltage of 1V, and a switching frequency of 250,000 Hz, 0.55375 W can be saved if the gate source voltage that is applied to the gate is 10V instead of 5V. As can be seen from the above formulas, the loss difference will vary depending on the output current, the duty cycle (i.e., the input voltage), and the switching frequency.

Next, determining a total gate drive loss and a conduction loss for a low-side MOSFET where the output current is 5 A rather than 30 A will be described. The change in output currency will not affect the calculation of the total gate drive loss at gate source voltage of either 5V or 10V. Thus, the following total gate drive loss values, as calculated above, will be used:

$$PtotalgatedriveLS(5V) = 0.03125 \text{ W}$$

$$PtotalgatedriveLS(10V) = 0.1375 \text{ W}$$

For a gate source voltage of 5V, a conduction loss for the low-side MOSFET can be calculated as follows:

Iout=5 A

RdsonLS(5V)=0.003Ω

DutyLS12=1−(Vout/Vin)

DutyLS12=1−(1V/12 V)

DutyLS12=0.91667

PconductionLS(5V)=Iout$^2$·RdsonLS(5V)·DutyLS12

PconductionLS(5V)=(5 A)$^2$·(0.003Ω)·(0.91667)

PconductionLS(5V)=0.06875 W

A conduction loss and total gate drive loss for a low-side MOSFET can then be combined as follows:

CombinedLSLosses(5V)=PconductionLS(5V)+PtotalgatedriveLS(5V)

CombinedLSLosses(5V)=0.06875 W+0.03125 W

CombinedLSLosses(5V)=0.1 W

For a gate source voltage of 10V rather than 5V, a conduction loss for the low-side MOSFET can be calculated as follows:

Iout=5 A

RdsonLS(10V)=0.0022Ω

DutyLS12=1−(Vout/Vin)

DutyLS12=1−(1V/12 V)

DutyLS12=0.91667

PconductionLS(10V)=Iout$^2$·RdsonLS(10V)−DutyLS12

PconductionLS(10V)=(5 A)$^2$·(0.0022Ω)·(0.91667)

PconductionLS(10V)=0.05042 W

A conduction loss and total gate drive loss for a low-side MOSFET can then be combined as follows:

CombinedLSLosses(10V)=PconductionLS(10V)+PtotalgatedriveLS(10V)

CombinedLSLosses(10V)=0.05042 W+0.1375 W

CombinedLSLosses(10V)=0.18792 W

The power loss difference that occurs when a gate is driven by a gate source voltage of 5V versus a gate source voltage of 10V can be calculated as follows:

LossDifference=CombinedLSLosses(5V)−CombinedLSLosses(10V)

LossDifference=0.05042 W−0.18792 W

LossDifference=−0.08792V

Thus, at an output current of 30 A, an input voltage of 12V, an output voltage of 1V, and a switching frequency of 250,000 Hz, 0.08792 W can be saved if the gate source voltage that is applied to the gate is 5V instead of 10V. As can be seen from the above formulas, the loss difference will vary depending on the output current, the duty cycle (i.e., the input voltage), and the switching frequency.

Figure 6:
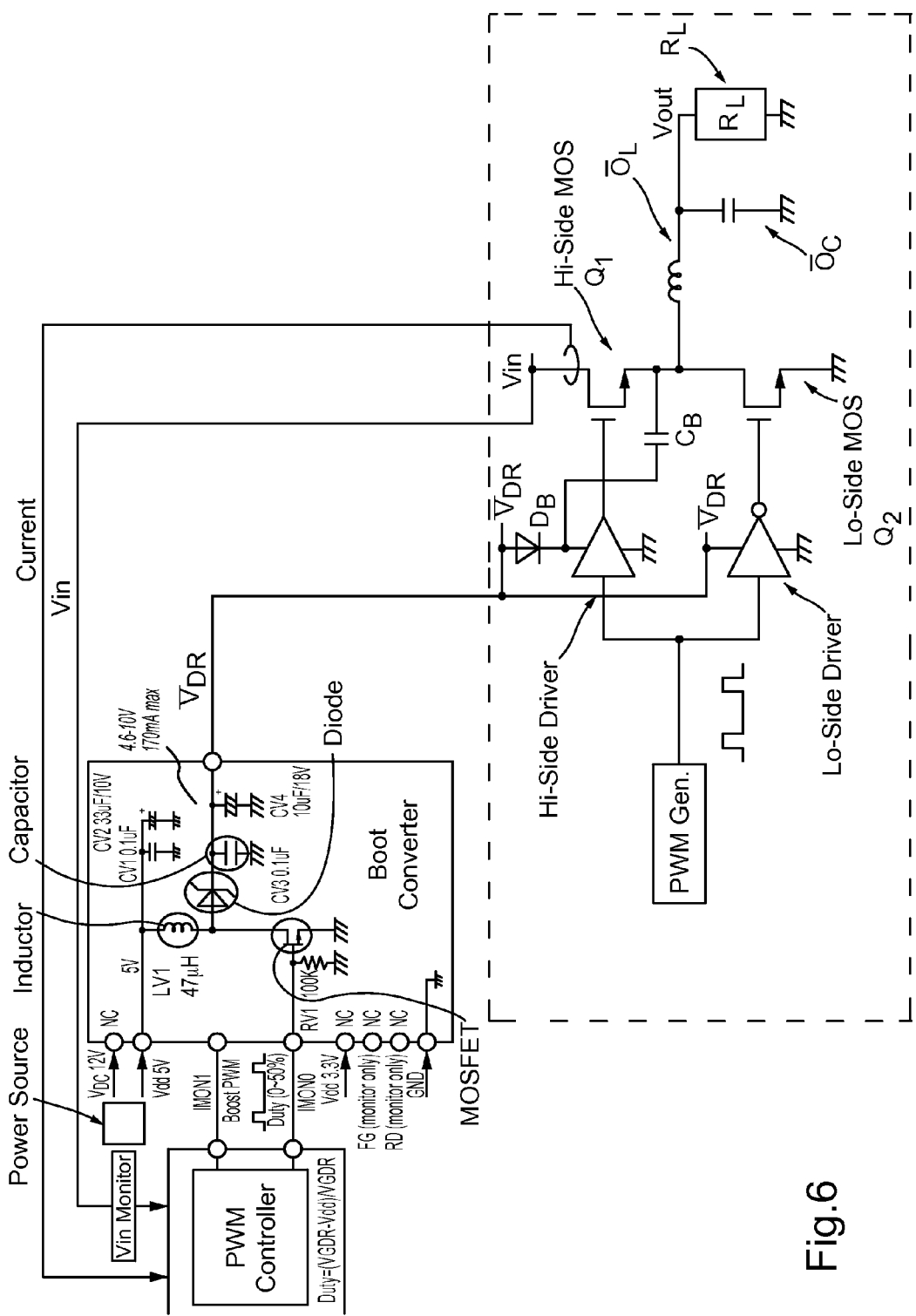
FIG. 6 illustrates an apparatus according to an embodiment of the invention.

FIG. 6 illustrates an apparatus according to an embodiment of the invention. The apparatus includes a microprocessor-based PWM controller. The apparatus also includes a boost converter. The apparatus also includes a DC-DC converter. In the illustrated embodiment, the DC-DC converter is a synchronous step-down DC-DC converter similar to the synchronous step-down DC-DC converter illustrated in FIG. 1.

According to the embodiment, as previously described in relation to FIG. 1, the DC-DC converter is configured to receive an input voltage (identified in FIG. 6 as "$V_{IN}$") and produce an output voltage (identified in FIG. 6 as "$V_{OUT}$") and an output current (identified in FIG. 6 as "current") using a drive voltage (identified in FIG. 6 as "$V_{DR}$"), where the output voltage is lower than the input voltage. As illustrated in FIG. 6, the DC-DC converter includes a pulse-width modulation ("PWM") generator (identified in FIG. 6 as "PWM Gen") configured to generate a PWM signal. The DC-DC converter also includes a high-side driver (identified in FIG. 6 as "Hi-Side Driver"), a low-side driver (identified in FIG. 6 as "Lo-Side Driver"), a high-side MOSFET (identified in FIG. 6 as "Hi-Side MOSFET"), and a low-side MOSFET (identified in FIG. 6 as "Lo-Side MOSFET"). The DC-DC converter also includes a diode (identified in FIG. 6 as "$D_B$"), a capacitor (identified in FIG. 6 as "$C_B$"), and an output inductor (identified in FIG. 6 as "$R_Z$"). Together, diode $D_B$ and capacitor $C_B$ are configured to create a voltage $V_{DR}+V_{IN}$, which the high-side driver can use to turn on the high-side MOSFET. Output inductor $R_Z$ is further configured to generate the voltage output of the high-side MOSFET and the low-side MOSFET as voltage $V_{OUT}$.

Furthermore, according to the embodiment, the microprocessor-based PWM controller is configured to monitor input voltage $V_{IN}$ and the output current. Based on the monitored input voltage $V_{IN}$, and the monitored output current, the microprocessor-based PWM controller is further configured to generate a pulse-width modulation signal to control the boost converter to generate a drive voltage in order to maximize the power efficiency of the DC-DC converter. In other words, the microprocessor-based PWM controller is further configured to generate the pulse-width modulation signal that controls the boost converter to generate a drive voltage that minimizes the power loss of the DC-DC converter. According to the embodiment, the microprocessor is configured to determine an optimal drive voltage based on the monitored input voltage $V_{IN}$, and the monitored output current ("current") using the formulas previously described in relation to FIGS. 3-5. In an embodiment of the invention, the microprocessor is configured to calculate one or more formulas to determine the optimal drive voltage. In an alternative embodiment, the microprocessor is configured to perform a lookup in a table, or determine by formula-based calculation, in order to determine the optimal drive voltage.

According to the embodiment, once the microprocessor has determined the optimal drive voltage, the microprocessor-based PWM controller can generate (or not generate) a pulse-width modulation signal to control the boost converter to generate the optimal drive voltage. More specifically, if the microprocessor-based PWM controller determines that the boost converter needs to boost a drive voltage to reach the optimal drive voltage, the microprocessor-based PWM controller can generate a PWM signal to control the boost converter to boost the drive voltage accordingly. Alternatively, if the microprocessor-based PWM controller determines that the boost converter does not need to boost a drive voltage, as the drive voltage is already at the optimal drive voltage, the microprocessor-based PWM controller does not generate the PWM signal, so that the boost converter does not boost the drive voltage.

While in the embodiment, the microprocessor is configured to determine an optimal drive voltage based on the monitored input voltage $V_{IN}$, and the monitored output current, in alternative embodiments, the microprocessor is configured to determine the optimal drive voltage based on additional factors. For example, the microprocessor can be configured to determine the optimal drive voltage based on a switching frequency of the DC-DC converter, an output voltage of the DC-DC converter, and a temperature of the DC-DC converter.

Furthermore, according to the embodiment, the boost converter is configured to include a power source, an inductor, an n-channel MOSFET (identified in FIG. 6 as "MOSFET"), a Schottky barrier diode (identified in FIG. 6 as "Diode") and a capacitor. The power source of the boost converter is configured to generate a drive voltage. In the illustrated embodiment, the power source is configured to generate a drive voltage Vdd of 5V. The Schottky barrier diode and capacitor are each configured to provide the drive voltage to the high-side driver and low-side driver of the DC-DC converter. When the PWM controller generates a PWM signal, the boost converter is configured to receive the PWM signal using the n-channel MOSFET and the inductor, and is configured to boost the drive voltage using the n-channel MOSFET and the inductor. Specifically, the boost converter is configured to boost the drive voltage based on a duty cycle of the PWM controller, using the below formula:

$$V_{DR}=5V\cdot(1+Dh/(1-Dh))-V_f$$

where $V_{DR}$ is a drive voltage, and Dh is a duty cycle of the PWM controller, with a value selected from 0 to 0.5, and $V_f$ is a Schottky barrier diode forwarding voltage with a value of approximately 0.3V.

For example, in the case of Dh=0 (i.e., when the PWM controller does not generate a PWM signal), $V_{DR}$=4.7V. However, in the case of Dh=0.5, $V_{DR}$=9.7V Thus, according to an embodiment of the invention, when an output current is such that a total switching loss of the DC-DC converter is greater than a total conduction loss of the DC-DC converter, then the PWM controller does not generate a PWM signal, and thus, the boost converter does not boost the drive voltage from its original voltage of 4.7V. However, when an output current is such that a total switching loss of the DC-DC converter is equal to or less than a total conduction loss of the DC-DC converter, then the PWM controller can generate a PWM signal that controls the boost converter to boots the drive voltage from its original voltage of 5V to a drive voltage where a total power loss of the DC-DC converter is minimized.

Figure 7:
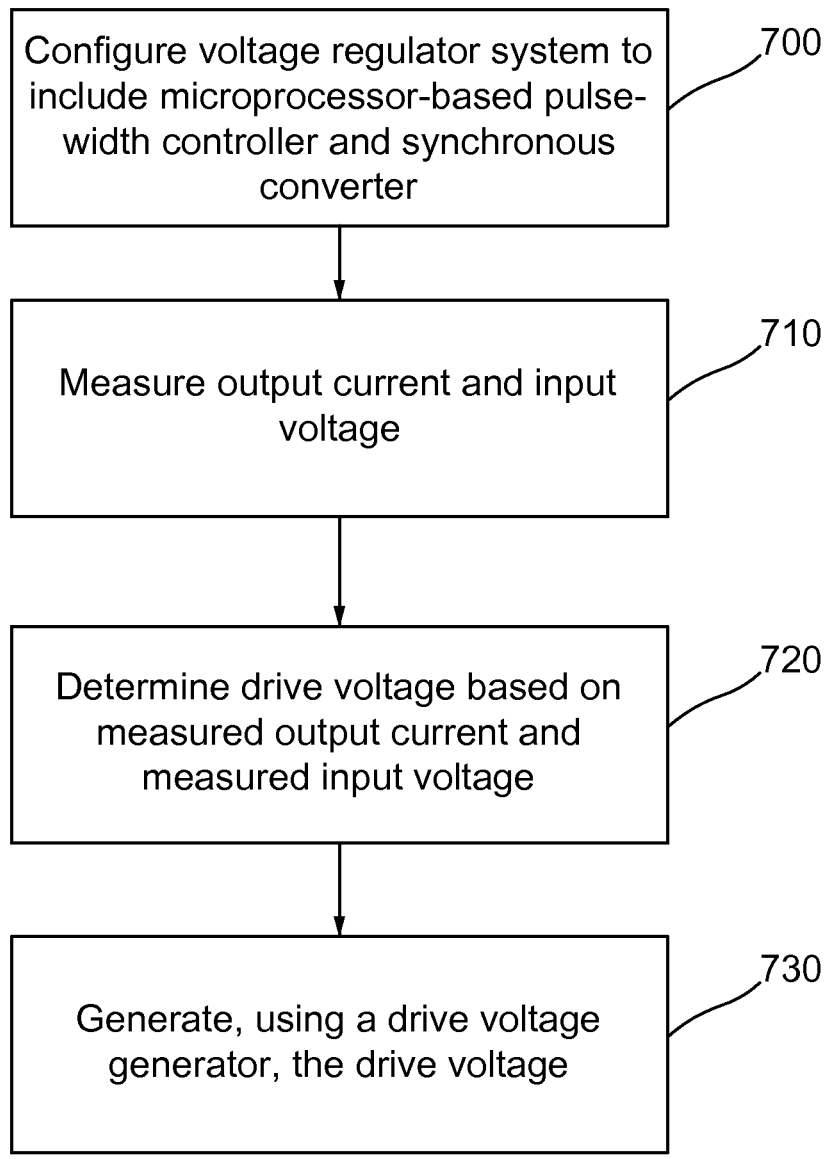
FIG. 7 illustrates a method according to an embodiment of the invention.

FIG. 7 illustrates a method according to an embodiment of the invention. According to the embodiment, at step 700, a voltage regulator system is configured to include a microprocessor-based pulse-width modulation controller and a synchronous converter. At step 710, an output current and input voltage are each measured. At step 720, a drive voltage is determined based on the measured output current and the measured input voltage. At step 730, a drive voltage generator generates the drive voltage determined at step 720.

Figure 8:
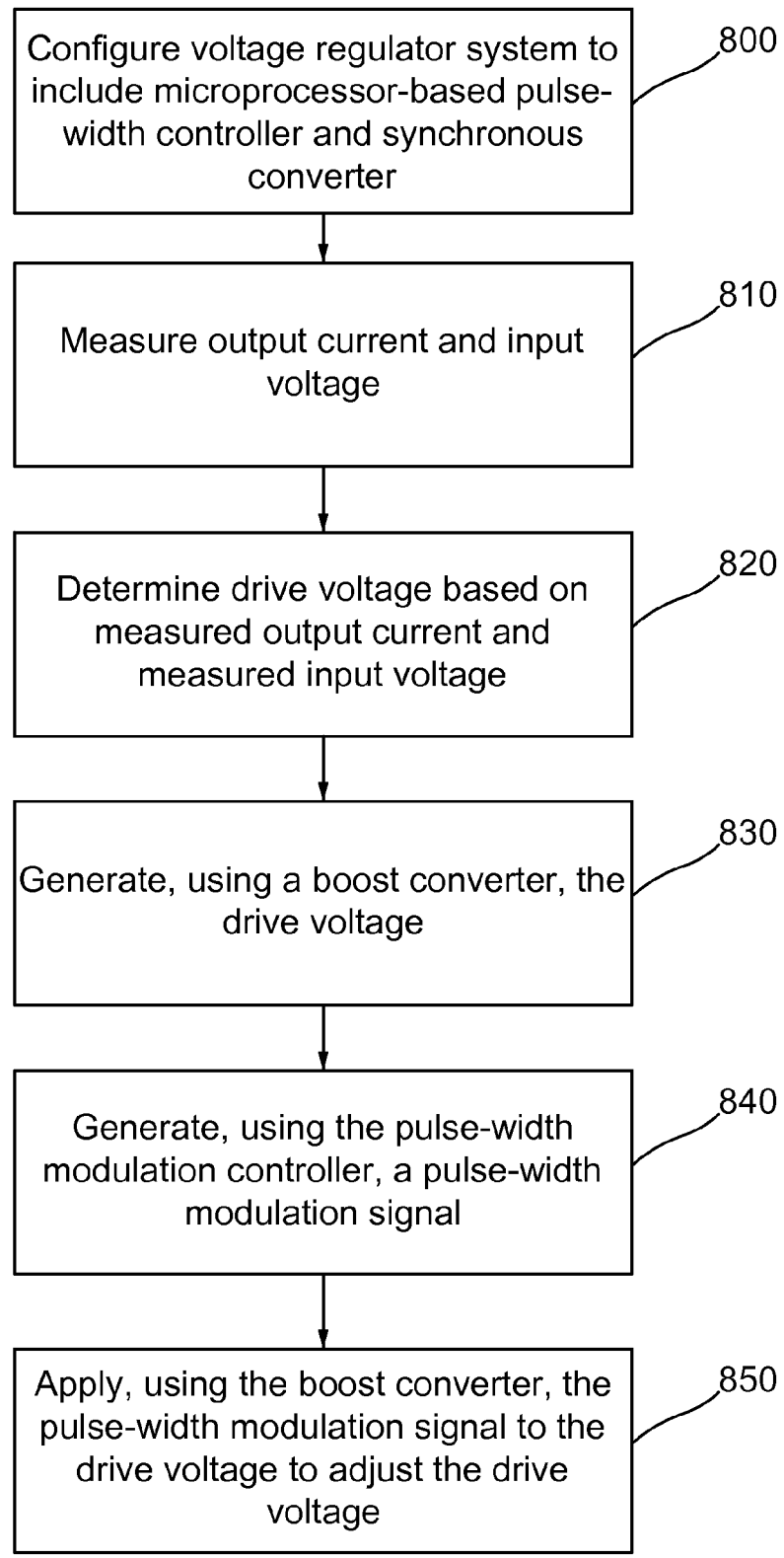
FIG. 8 illustrates another method according to an embodiment of the invention.

FIG. 8 illustrates another method according to an embodiment of the invention. According to the embodiment, at step 800, a voltage regulator system is configured to include a microprocessor-based pulse-width modulation controller and a synchronous converter. At step 810, an output current and input voltage are each measured. At step 820, a drive voltage is determined based on the measured output current and the measured input voltage. At step 830, a boost converter generates the drive voltage. At step 840, a pulse-width modulation generator generates a pulse-width modulation signal. At step 850, the boost converter applies the pulse-width modulation signal to the drive voltage to adjust the drive voltage.

Figure 9:
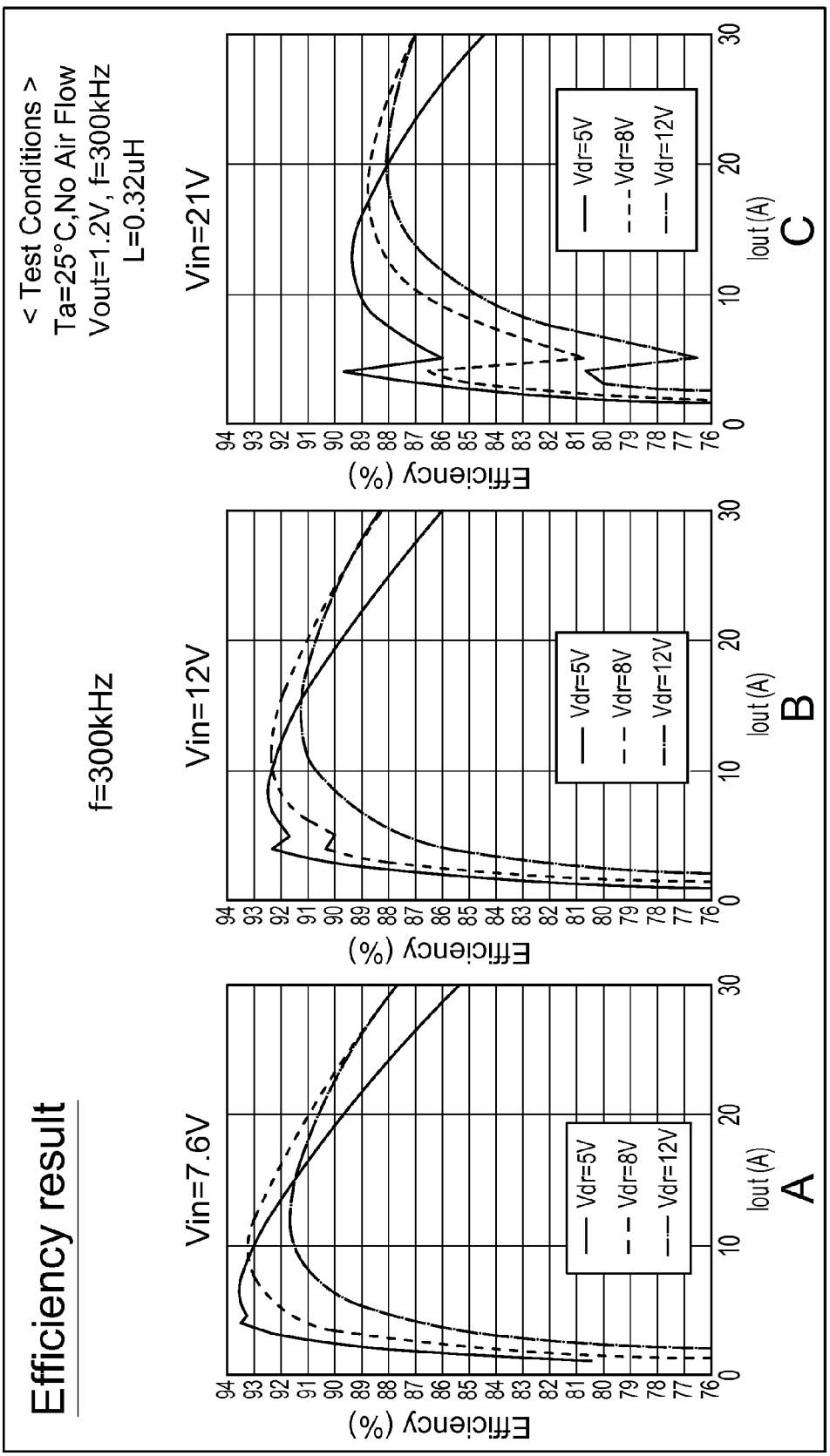
FIG. 9 illustrates three graphs which correlate an output current of a direct-current to direct-current converter with a power efficiency of the direct-current to direct-current converter for three different input voltages according to an embodiment of the invention.

FIG. 9 illustrates three graphs which correlate an output current of a DC-DC converter with a power efficiency of the DC-DC converter for three different input voltages according to an embodiment of the invention. Each of the three graphs illustrate a power efficiency of a DC-DC converter under a set of test conditions. Specifically, the test conditions include an overall temperature of 25° C., no air flow, an output voltage of 1.2V, a switching frequency of 300 kHz, and an inductance of 0.32 μH. Furthermore, graph A illustrates a power efficiency of a DC-DC converter under the set of test conditions, with an input voltage of the DC-DC converter of 7.6V, graph B illustrates a power efficiency of a DC-DC converter under the set of test conditions, with an input voltage of the DC-DC converter of 12V, and graph C illustrates a power efficiency of a DC-DC converter under the set of test conditions, with an input voltage of the DC-DC converter of 21V. The power efficiency of the DC-DC converter is calculated using the formulas previously described in relation to FIGS. 3-5.

Each of the three graphs illustrate a power efficiency of a DC-DC converter under the set of test conditions for three drive voltages. Specifically, each graph illustrates a power efficiency of the DC-DC converter for a drive voltage of 5V (indicated by a solid line in FIG. 9), a drive voltage of 8V (indicated by a dashed line in FIG. 9), and a drive voltage of 12V (indicated by a dashed and dotted line in FIG. 9). As can be seen, for example, in graph A, for each output current value, there are three power efficiency values, a first power efficiency value for a drive voltage of 5V, a second power efficiency value for a drive voltage of 8V, and a third power efficiency value for a drive voltage of 12V. The three power efficiency values are all different which indicate that a particular drive voltage maximizes the power efficiency of the DC-DC converter, and thus, minimizes the power loss of the DC-DC converter.

As can be seen in graph A of FIG. 9, there is a range of output current values starting from 0 A and moving to the right of graph A, where the power efficiency value associated with the drive voltage of 5V is the highest power efficiency. However, after a first "cross-point" (which is defined as a point where two or more power efficiency curves intersect) in graph A, the power efficiency value associated with the drive voltage of 5V is no longer the highest power efficiency, and instead, the power efficiency value associated with the drive voltage of 8V is the highest efficiency. This is because, in the lower current region, also referred to as a "light load," the most dominant part of the power loss is a switching loss, rather than a conduction loss. In contrast, in the middle current region, also referred to as a "medium load," the most dominant part of the power loss is a conduction loss, rather than a switching loss, and the increased drive voltage can assist in reducing a saturation resistance, and thus, can assist in reducing a conduction loss. This reduction in conduction loss can increase the power efficiency.

Furthermore, after a second cross-point in graph A, the power efficiency value associated with the drive voltage of 8V is no longer the highest power efficiency, and instead, the power efficiency value associated with the drive voltage of 12V is the highest efficiency. This is because, in a high current region, also referred to as a "heavy load," a higher drive voltage is needed to further reduce the saturation resistance, and thus, further reduce the conduction loss. Thus, for a specific input voltage, the drive voltage that produces the highest power efficiency depends on the output current.

As illustrated in FIG. 9, graphs B and C show power efficiency values that are similar to the power efficiency values of graph A. However, one important difference between graphs A, B, and C, is that the first and second cross-points are different for each graph. More specifically, in graph B, two or more power efficiency curves intersect at output current values that are different from graphs A and C, and in graph C, two or more power efficiency curves interest at output current values that are different from graphs A and B. Thus, the cross-point shift from graph A (which represents an input voltage of 7.6V), to graph B (which represents an input voltage of 12V), to graph C (which represents an input voltage of 21V). This means that a cross-point depends on an input voltage as well as an output current, and in order to determine a highest power efficiency, one must take into consideration both an output current and an input voltage.

Figure 10:
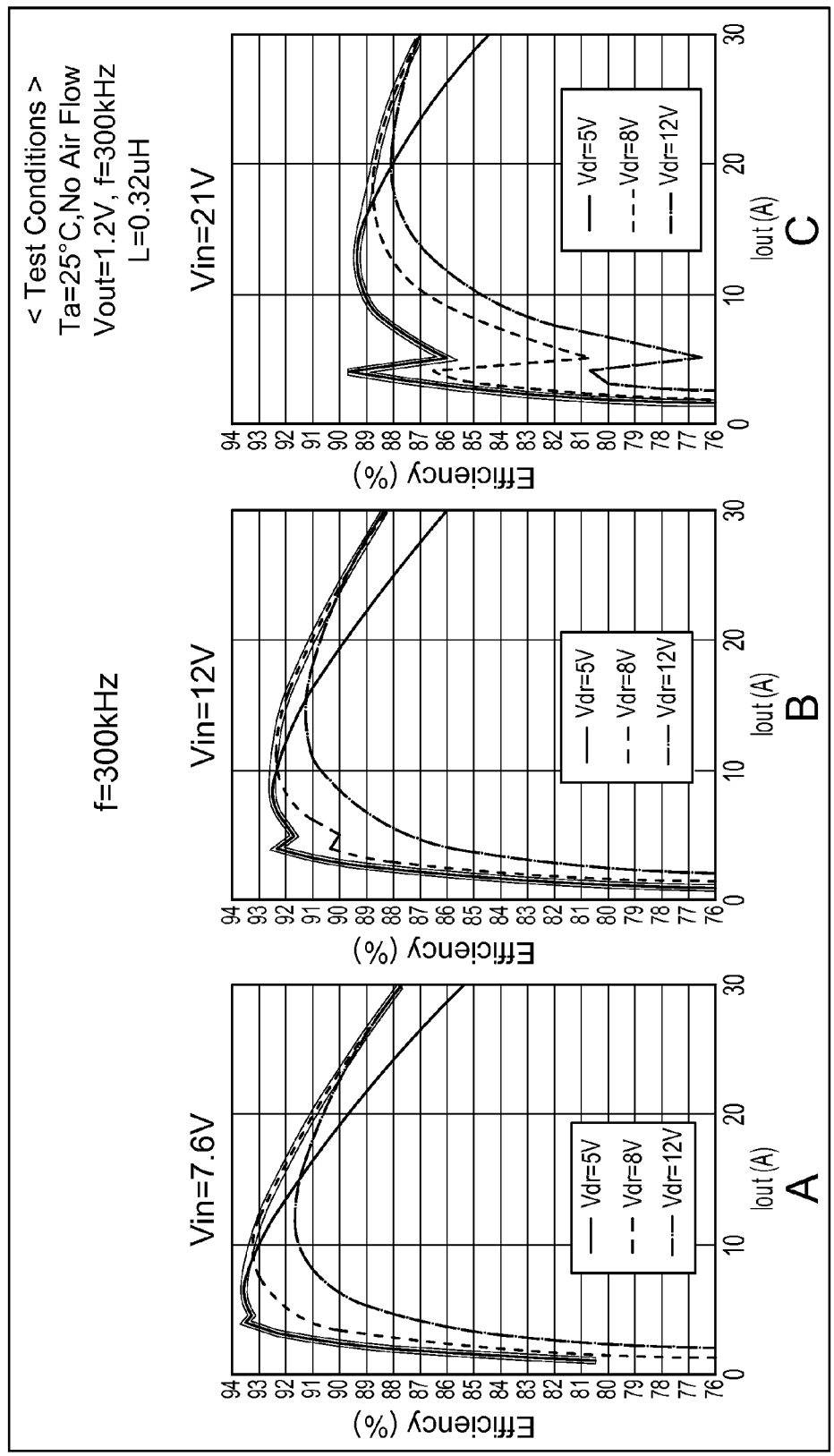
FIG. 10 illustrates advantages according to an embodiment of the invention utilizing the three correlation graphs from FIG. 9.

FIG. 10 illustrates advantages according to an embodiment of the invention utilizing the three correlation graphs from FIG. 9. Specifically, FIG. 10 illustrates the three correlation graphs from FIG. 9, but for each of graphs A, B, and C, the highest power efficiency for each output current value of the graph has been highlighted. This shows that by varying the drive voltage based on an output current and an input voltage, a maximum power efficiency can be realized. Thus, according to an embodiment of the invention, a computer system, such as an NBPC system, can realize a maximum power loss efficiency not only during a heavy load, but also during a light load, by varying a drive voltage generated for a MOSFET. Achieving a maximum power loss efficiency during a light load can allow a battery power source of a computer system, such as a lithium battery, to operate longer. Achieving a maximum power loss efficiency during a heavy load can reduce a size of a heat sink, and reduce a strength needed by a built-in cooling system, such as a cooling fan.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. An apparatus, comprising:
    a DC-DC converter comprising a pulse-width modulation (PWM) generator that generates a first PWM signal;
    wherein the DC-DC converter is configured to generate an output voltage that depends on a first input voltage to the DC-DC converter and a duty cycle of the first PWM signal;
    a device for measuring the first input voltage at a point in time;
    a device for measuring an output current of the DC-DC converter at the point in time;
    a processor based PWM controller that calculates a second duty cycle as a function of the measured first input voltage and the measured output current of the DC-DC converter;
    wherein the processor based PWM controller is configured to generate a second PWM signal having the second duty cycle;
    a boost converter coupled to receive the second PWM signal and configured to generate a drive voltage for the DC-DC converter,
    wherein a magnitude of the drive voltage depends on the second duty cycle of the second PWM signal.

2. The apparatus of claim 1 wherein the DC-DC converter comprises a first transistor, a second transistor, a first driver, and a second driver, wherein the first driver is configured to receive the drive voltage, and wherein the first driver is configured to drive a gate of the first transistor using the drive voltage.

3. The apparatus of claim 1, wherein the second duty cycle of the second PWM signal depends on a measured switching frequency of the DC-DC converter.

4. The apparatus of claim 1, wherein the second duty cycle of the second PWM signal depends on a measured temperature of the DC-DC converter.

5. The apparatus of claim 1 wherein the boost converter comprises an inductor, a diode, a capacitor, and a transistor, and wherein the transistor is configured to receive the second PWM signal at a gate thereof.

6. The apparatus of claim 5 wherein the transistor is configured to receive a second input voltage that is different from the first input voltage, and wherein the magnitude of the drive voltage depends on the second input voltage.

7. A method, comprising:
    generating a first PWM signal having a first duty cycle;
    a first DC-DC converter generating an output voltage with a magnitude that depends on a first input voltage and the first duty cycle of the first PWM signal;
    measuring the first input voltage and an output current of the first DC-DC converter at a first point in time;
    calculating a second duty cycle using the first input voltage and the output current measured at the first point in time;
    generating a second PWM signal having the calculated second duty cycle;
    a second DC-DC converter generating a drive voltage for the first DC-DC converter wherein a magnitude of the drive voltage depends on the second duty cycle of the second PWM signal.

8. The method of claim 7, wherein the first DC-DC converter comprises a first transistor, a second transistor, a first driver, and a second driver.

9. The method of claim 7, wherein the second duty cycle of the second PWM signal depends on a switching frequency of the first DC-DC converter.

10. The method of claim 7, wherein the second duty cycle of the second PWM signal depends on a temperature of the first DC-DC converter.

11. The method of claim 7 further comprising:
    measuring the first input voltage and the output current of the DC-DC converter at another point in time;

calculating a third duty cycle using the first input voltage and the output current measured at the other point in time, wherein the first and second duty cycles are different;

generating a third PWM signal having the calculated third duty cycle;

the second DC-DC converter generating a second drive voltage for the first DC-DC converter wherein a magnitude of the second drive voltage depends on the third duty cycle.

12. The method of claim 7 wherein the second DC-DC converter comprises a boost converter.

13. A method comprising:

a battery generating a first voltage that drops as the battery discharges;

a first DC-DC converter generating an output voltage with a magnitude that varies with a first duty cycle of a first PWM signal;

a processor based controller generating a second duty cycle that increases as the first voltage decreases;

the processor based controller generating a second PWM signal having the second duty cycle;

a second DC-DC converter generating a drive voltage for the first DC-DC converter, wherein a magnitude of the drive voltage increases as the second duty cycle increases.

14. The method of claim 13, wherein the second duty cycle of the second PWM signal depends on a switching frequency of the first DC-DC converter.

15. The method of claim 14, wherein the second duty cycle of the second PWM signal depends on a temperature of the first DC-DC converter.

16. The method of claim 15, wherein the second duty cycle of the second PWM signal depends on an output current of the first DC-DC converter.

17. The method of claim 13 wherein the second duty cycle is zero when the battery is fully charged, and wherein the second duty cycle is greater than zero when the battery is not fully charged.

18. The method of claim 17 wherein the second DC-DC converter comprises a boost converter, wherein the boost converter comprises a transistor that is controlled by the second PWM signal.

* * * * *